United States Patent
Zalis et al.

(10) Patent No.: US 9,305,052 B2
(45) Date of Patent: Apr. 5, 2016

(54) SYSTEM AND METHOD FOR QUERIED PATIENT ABSTRACT

(75) Inventors: Michael E. Zalis, Newtonville, MA (US); Mitchell A. Harris, West Newton, MA (US)

(73) Assignee: The Massachusetts General Physicians Organization, Boston, MA (US)

( * ) Notice: Subject to any disclaimer, the term of this patent is extended or adjusted under 35 U.S.C. 154(b) by 528 days.

(21) Appl. No.: 13/696,932

(22) PCT Filed: May 12, 2011

(86) PCT No.: PCT/US2011/036221
§ 371 (c)(1),
(2), (4) Date: Mar. 21, 2013

(87) PCT Pub. No.: WO2011/143405
PCT Pub. Date: Nov. 17, 2011

(65) Prior Publication Data
US 2013/0198225 A1    Aug. 1, 2013

Related U.S. Application Data

(60) Provisional application No. 61/333,947, filed on May 12, 2010.

(51) Int. Cl.
| G06F 7/00 | (2006.01) |
| G06F 17/30 | (2006.01) |
| G06Q 10/10 | (2012.01) |
| G06Q 50/22 | (2012.01) |

(52) U.S. Cl.
CPC .......... *G06F 17/30424* (2013.01); *G06Q 10/10* (2013.01); *G06Q 50/22* (2013.01)

(58) Field of Classification Search
CPC .. G06Q 10/10; G06Q 50/22; G06F 17/30424; G06F 17/30663; G06F 17/30616; G06F 17/30643
See application file for complete search history.

(56) References Cited

U.S. PATENT DOCUMENTS

| 7,624,027 | B1 * | 11/2009 | Stern et al. ................. 705/2 |
| 2002/0046346 | A1 | 4/2002 | Evans |
| 2005/0060195 | A1 * | 3/2005 | Bessette et al. ............ 705/2 |
| 2006/0235881 | A1 | 10/2006 | Masarie et al. |
| 2009/0012822 | A1 | 1/2009 | Ross et al. |
| 2010/0088117 | A1 | 4/2010 | Belden et al. |
| 2010/0106522 | A1 * | 4/2010 | Cooper et al. .............. 705/3 |
| 2011/0213655 | A1 * | 9/2011 | Henkin et al. ........... 705/14.49 |

OTHER PUBLICATIONS

International Search Report and Written Opinion under date of mailing of Oct. 26, 2011 in connection with PCT/US2011/036221.

* cited by examiner

*Primary Examiner* — Azam Cheema
(74) *Attorney, Agent, or Firm* — Quarles & Brady, LLP (57) ABSTRACT

A system and method for generating a patient abstract containing data about a patient selected from the patient's medical records is presented. A medical order for a patent is analyzed and at least one term is extracted from the medical order. Based upon the extracted term, at least one medical concept related to an extracted term is identified. Then at least one medical data element related to an identified medical concept is identified. A database containing at least a portion of the patient's medical records is queried for the identified at least one medical data element, and at least a portion of a result from the query is displayed, for example, via a user interface.

14 Claims, 7 Drawing Sheets

SYSTEM AND METHOD FOR QUERIED PATIENT ABSTRACT

CROSS REFERENCE TO RELATED APPLICATIONS

This application represents the national stage entry of PCT International Application No. PCT/US2011/036221 filed on May 12, 2011 which claims the benefit of U.S. Provisional Application Ser. No. 61/333,947 filed May 12, 2010. The contents of both of these applications are hereby incorporated by reference as if set forth in their entirety herein.

FIELD OF THE INVENTION

The present invention relates to systems and methods for querying a patient's medical records and, more particularly, to a system and method for using terms in a medical order or other input to select and display excerpts from the patient's medical record, where the excerpts include information relevant to the order.

BACKGROUND OF THE INVENTION

When a physician refers a patient to a specialist, such as a radiologist or oncologist, the referring physician writes a medical order providing instructions to the specialist. The order typically includes minimal information, usually formatted as unstructured text, commonly called a "history" or "question" that describes an ongoing problem, identifies a suspected medical problem, or poses a question to the specialist. For example, the ordering physician may suspect the patient has breast cancer and may ask in a written medical order that a radiologist attempt to rule out metastases. In another example, the patient may have a recent history of abdominal pain, and the referring physician may seek an opinion regarding whether the patient has an infection. In some cases, the written medical order will include instructions for the specialist to perform a particular study, though in other cases it is up to the specialist to review the written medical order and perform any studies useful in answering the physician's posed questions.

The specialist's studies may include X-ray images of the patient, quantitative laboratory results, such as blood lead level or standardized uptake values measured by positron emission tomography (PET), or the like. The specialist interprets the studies to confirm or refute the suspected medical problem or to answer the question posed in the order.

Background information about the patient and the patient's medical history can aid the specialist in interpreting the results of any performed studies. For example, knowing that the patient has a recent history of elevated white blood count may cause the specialist to consider a particular interpretation of a study to be more likely than if the patient had a normal white blood count.

In many cases, though, the specialist has no prior knowledge of the patient or the patient's medical history, and the medical order usually provides the specialist with little or no background information. As a result, the specialist is often required to interpret the study with only the information written in the medical order. Otherwise, the specialist is required to take additional time to access the patient's medical records and search for data that may be relevant to the question or study at hand.

These searches of a patient's longitudinal medical record (LMR) can be extremely time consuming. For example, in a radiological study, LMR searching can consume 20-53% of the total interpretation time of the study. Similar LMR searches may be performed in 27-64% of all Abdominal-Pelvic CT (ABP-CT), Transvaginal Pelvic Ultrasound (TV-US), and Brain MRI (B-MRI) studies. In a relatively large hospital, every week many hundreds of these studies may be performed. Therefore, a large amount of time and health care money is spent manually searching patient medical records for ancillary medical data.

SUMMARY OF THE INVENTION

The present invention relates to systems and methods for querying a patient's medical records and, more particularly, to a system and method for using terms in a medical order or other input to select and display excerpts from the patient's medical record, where the excerpts include information relevant to the medical order.

In one implementation, the present invention is a computer system for generating a patient abstract containing data about a patient selected from the patient's medical records. The computer system includes a system configured to read a medical order for the patient into an electronically-readable memory, and a character recognition system in communication with the electronically-readable memory. The character recognition system is configured to retrieve the image of the medical order from the electronically-readable memory, convert the medical order into machine-readable text, and store the machine-readable text in the electronically-readable memory. The computer system includes a processor in communication with the electronically-readable memory. The processor is configured to retrieve at least a portion of the machine-readable text from the electronically-readable memory, extract a first term from the at least a portion of the machine-readable text, and retrieve an ontology from at least one of the electronically-readable memory and an electronically-readable database. The ontology defines relationships between a plurality of terms, a plurality of medical concepts, and a plurality of data elements. The processor is configured to use the ontology to identify at least one medical concept related to the at least one term extracted from the written medical order, use the at least one medical concept and the ontology to identify at least one medical data element related to the at least one medical concept, and access, via an electronic communications network, the medical records of the patient to retrieve data associated with the at least one medical data element. The computer system includes a user interface configured to display at least a portion of the data associated with the at least one medical data element retrieved from the medical records.

In other implementations, the present invention is a method for generating a patient abstract containing data about a medical history of a patient. That data is selected from the patient's medical records for relevancy to a written medical order. The method includes receiving a written medical order for the patient, extracting at least one term from the written medical order in an electronically readable form, and retrieving an ontology from at least one of an electronically-readable database and an electronically-readable memory. The ontology defines relationships between a plurality of terms, a plurality of medical concepts, and a plurality of data elements. The method includes using the ontology to identify at least one medical concept related to the at least one term extracted from the written medical order, using the at least one medical concept and the ontology to identify at least one medical data element related to the at least one medical concept, and accessing the medical records of a patient to retrieve data associated with the at least one medical data element. The method includes using a user interface to display at least a portion of the data associated with the at least one medical data element retrieved from the medical records.

In other implementations, the present invention is a method for generating a patient abstract containing data about a patient selected from the patient's medical records. The method includes extracting at least one term from a medical order for the patient, identifying at least one medical concept related to an extracted term, and identifying at least one medical data element related to an identified medical concept. The method includes querying a database containing at least a portion of the patient's medical records for the identified at least one medical data element, and displaying at least a portion of a result from the query.

In other implementations, the present invention is a system for generating a patient abstract containing data about a patient selected from the patient's medical records. The system includes means for extracting at least one term from a medical order for the patient, means for identifying at least one medical concept related to an extracted term, and means for identifying at least one medical data element related to an identified medical concept. The system includes means for querying a database containing at least a portion of the patient's medical records for the identified at least one medical data element, and means for displaying at least a portion of a result from the query.

The foregoing and other aspects and advantages of the invention will appear from the following description. In the description, reference is made to the accompanying drawings which form a part hereof, and in which there is shown by way of illustration at least one embodiment of the invention. Such embodiment does not necessarily represent the full scope of the invention, however, and reference is made therefore to the claims and herein for interpreting the scope of the invention.

DETAILED DESCRIPTION

As will become apparent from the description provided below, a method and apparatus are disclosed for automatically generating a patient history abstract (also referred to herein as a "patient abstract", "abstract", or "queried patient abstract") that contains selected portions of a patient's medical history, or other information related to the patient. In one implementation, the patient information is anticipated to be of relevance to a specialist who will analyze a patient's study, perform a procedure or otherwise treat or diagnose the patient.

The method and apparatus can have utility in many different settings. For example, in one setting, a clinician refers a patient to a consulting physician, laboratory, treatment facility or the like and the referring clinician writes a medical order (or more simply an "order"). From information contained in the order, inferences are automatically drawn about the purpose for the order, including the nature of the patient's situation or condition. These inferences are then used to identify data items that may be present in the patient's medical records and that, if present, are likely to be of interest to a physician, laboratory technician, treatment provider or other person (collectively "specialist") who will interpret results of the study or otherwise diagnose, treat or perform a procedure on the patient. The patient's medical records are queried for the identified data items, and retrieved data items are displayed to the specialist in a patient abstract. The retrieved data items in the patient abstract may be displayed as excerpts from the patient's medical record. In some cases, hyperlinks associated with the displayed data items can be used by the specialist to retrieve and display surrounding, more complete, or additional data from the medical records or other sources.

Although the present system is described in terms of analyzing a medical order to identify data items that may be included in a patient abstract, the present system can be used in any application that calls for generating a patient abstract using input data where the input data identifies any number of symptoms or possible medical conditions of a patient, or requests that particular tests or examinations of a patient be performed. Accordingly, the terms "medical order", "written order," or "written medical order" should be interpreted broadly to include any written request for information that includes free-form written content and identifies any number of symptoms or possible medical conditions of a patient, or requests that particular tests or examinations of a patient be performed.

The patient abstract can be generated between the time a medical order is written and the time a specialist begins work on the order, for example by performing and evaluating patient studies, providing treatment, or performing a requested procedure. Using the patient abstract, the specialist can save time that would otherwise be occupied by deciding what background information to obtain about the patient and by querying numerous databases to retrieve the information from the patient's medical records. Additionally, because data is selected for inclusion in the patient abstract based upon information contained within the medical order, the abstract is likely to provide the specialist with highly relevant data in a compact form, thereby optimizing the specialist's reading time.

Additionally, because the system is rule based, the patient abstract includes data items that the specialist may not otherwise have requested, such as due to fatigue, lack of experience or error, or obscurity of the relationship between the reason for the medical order and the data item. Thus, the system may alert the specialist to useful background data that the specialist may otherwise have missed.

Furthermore, as more is learned about relationships among diseases, causes and ascertainable facts or diagnostic values, the rules may be augmented or updated to the benefit of users of the system.

In the present system, a patient abstract is generated based upon a medical order or other input containing information about a patient. The input is analyzed to generate inferences about the purpose of the medical order using rules identifying data that may be relevant to that purpose. The inferences may be drawn from a particular question presented in the medical order, or other text or information in the order.

Because a medical order may include a variety of words, phrases, or other information (collectively "terms") that refer to similar concepts, the present system uses a mapping to connect each term in the order to one or more concepts. Each concept can then be expanded to include related concepts or data points that can then be search for in the client's medical history. For example, the term "abdominal pain" may appear in a medical order. The medical order is processed, and the term "abdominal pain" can then be mapped to the various concepts including "abscess," "indigestion" and "appendicitis." Each identified concept can then be used to identify one or more data elements that may appear in a medical record. The patient's medical records can then be queried using the identified data elements, and results of the query are presented as a resulting patient abstract. Depending upon the presentation of the patient abstract, the results displayed in the patient abstract may include hyperlinks to surrounding or more complete data in the patient's medical record or other sources.

Ontology-Based Term/Concept/Data Element Mapping

To provide for the mapping of terms found in the medical order to a set of concepts, the present system uses an ontology. The ontology is a data model that represents a domain (in the present disclosure, the domain may include diagnostic or therapeutic medical information). Within a particular domain, the ontology identifies objects (e.g., terms, concepts, or data) that reside within that domain and specifies relationships between those objects. By categorizing the information presented by the ontology into three categories—terms, concepts, or data—the ontology can be simplified compared to other mapping structures that would map terms directly to data elements. By including the intermediary object of a 'concept' between terms and data elements, the mapping can be simplified as each term and data element will only be related a relatively small number of intermediary concepts. If the ontology only mapped terms to data elements, each term would be mapped to many data elements, and each data element would be mapping to each term resulting in possibly millions of interconnections. As such, the inclusion of the 'concepts' into the ontology described below acts to compress or otherwise simplify the ontology, making management and implementation of the ontology easier. For example, if a new term is introduced into the ontology, that term may only need to be connected to a small number of concepts, that, in-turn, connect to many data elements. Accordingly, the addition or removal of terms or data elements when using the ontology configuration described below is greatly facilitated.

Figure 1:
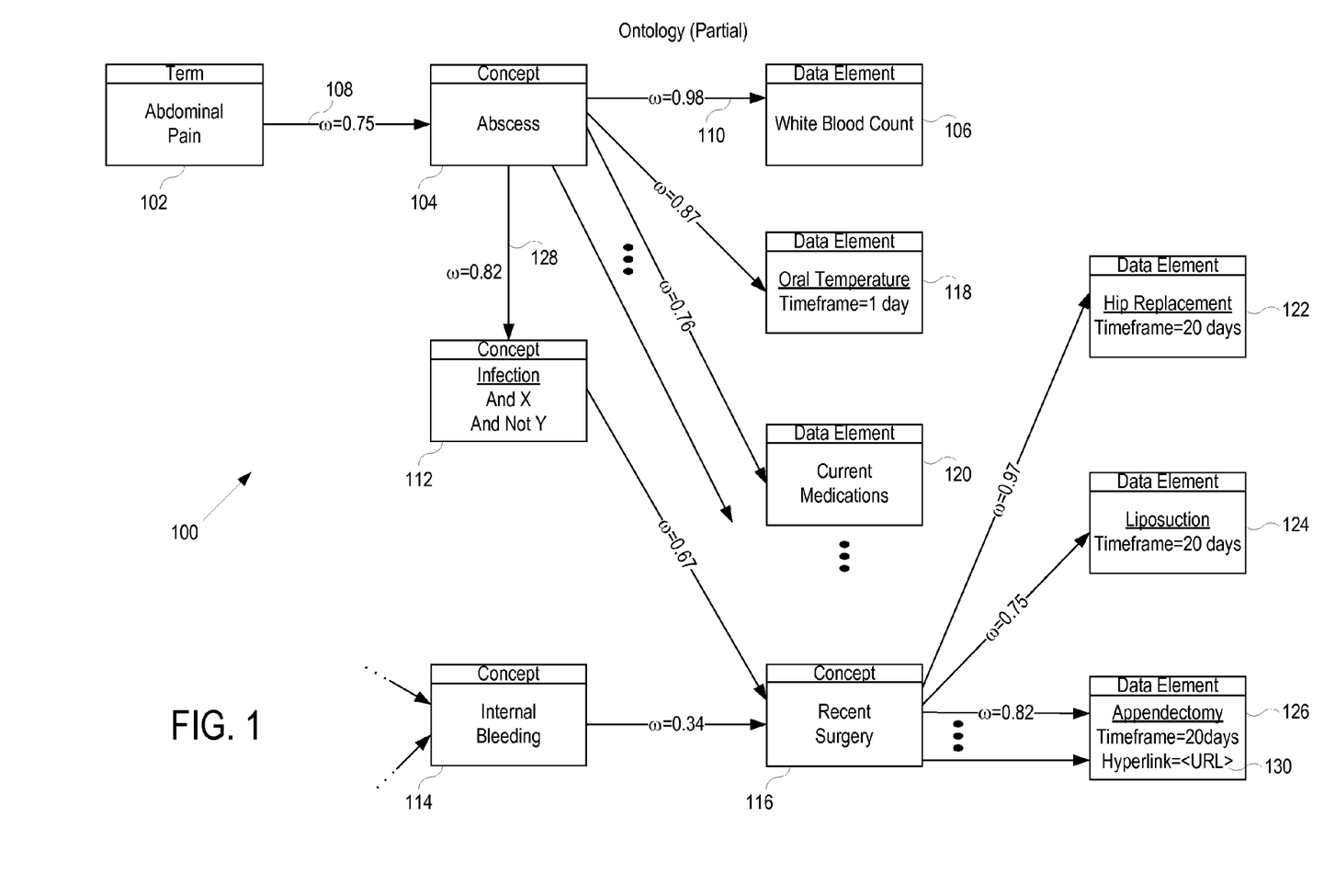
FIG. 1 is a block diagram illustrating a portion of an example ontology for use in conjunction with the present system.

FIG. 1 is an illustration of a portion of an exemplary ontology 100 that can be used in one implementation of the present system. Within FIG. 1, each block represents a term, concept, or data element (collectively "objects"). Block 102, for example, represents the term "abdominal pain," while block 104 represents the concept "abscess", and block 106 represents the data element "white blood count." Each term within the ontology may be directly related to one or more data elements or concepts, as indicated by arrows in FIG. 1 connecting term blocks to concept blocks, and each concept may be directly related to one or more other concepts and/or data element identifiers. For example, in ontology 100, the term "abdominal pain" 102 is directly related to the concept "abscess" 104, as indicated by arrow 108, and the concept "abscess" 104 is directly related to the data element identifier "white blood count" 106, as indicated by arrow 110.

Similarly, several objects within ontology 100 may be directly related to a single object. For example, both the concept "infection" 112 and the concept "internal bleeding" 114 are directly related to the concept "recent surgery" 116. Two objects are "indirectly related" if they are related to each other through at least one other object. For example, "abdominal pain" 102 is indirectly related to "infection" 112 and to "recent surgery" 116.

Starting with a term, such as "abdominal pain" 102, a set of directly and indirectly related concepts, such as "abscess" 104, "infection" 112 and "recent surgery" 116, can be identified using ontology 100. The identified concepts are said to be inferred from the term or from the medical order. Using concepts that are indirectly related to terms found in a medical order enlarges the scope of concepts found, and therefore the possible list of data items displayed, by the system.

A patient's medical records may contain a wide variety of laboratory data, reports, x-ray images, physician notes and the like. Some of this information may be structured numerical data. For example, a complete blood count (CBC) usually includes white blood cell count, white blood cell types, red blood cell count, hematocrit, etc. Other information in the medical records may be in the form of unstructured expository text, such as physician notes, family history records, etc.

A patient's medical records may be stored in a single database; however, more frequently, the medical records of a single patient are distributed across several databases. These databases may be physically located in disparate locations. Each of the locations may be associated with one or more of a plurality of different organizations, such as independent laboratories, hospitals, clinics and doctor offices, where the patient has been seen. A single organization may maintain more than one of these databases. For example, a hospital's radiology department may maintain a database of imaging studies (such as x-ray, ultrasound and computed tomography (CT) images and written analyses generated therefrom), and the hospital's blood laboratory may maintain a separate database containing blood studies.

Ontology 100 also includes blocks that represent data elements that may be found in a patient's medical records. For example, block 106 represents the data element "white blood count," block 118 represents the data element "oral temperature," block 120 represents a list of "current medications," block 122 represents "hip replacement" surgery 122, block 124 represents "liposuction" surgery, and block 126 represents "appendectomy." Each data element defines one or more of text strings, database columns, or other mechanisms allowing data corresponding to each data element to be retrieved from the patient's medical record.

A patient's medical records may, of course, contain multiple instances of a given data element. For example, the medical records may contain several white blood counts, each taken on a different day. However, the contents of ontology 100 are not related to the number of instances of a particular data element in a patient's medical records. Ontology 100 is used to identify one or more distinct data elements (such as "white blood count" or "liposuction") that are related to a given term (such as "abdominal pain"). Another portion of the system then queries the medical records databases to locate instances of the identified data element with the patient's medical record, if the databases contain any such instances.

Each concept in ontology 100 is mapped to one or more data elements that may be of relevance to a specialist conducting a study that relates to the concept. For example, if a specialist is conducting a study related to abdominal pain 102, the specialist may be concerned that the pain is caused by an abscess 128 or by an infection 112. With respect to the possibility of an abscess, the specialist is likely to find the patient's white blood count 106, oral temperature 118 and current medications 120 relevant to any analysis, because this information may make one diagnosis more likely than another. Similarly, with respect to the possibility of an infection 112 caused by a recent surgery 116, the specialist is likely to find it relevant if the patient has undergone a hip replacement 122, liposuction 124 or appendectomy 126.

Optionally, timeframes and/or other selection criteria or selection logic may be associated with a particular object within ontology 100. For example, each of the surgery data elements 122-126 shown in ontology 100 includes a defined timeframe. Only surgeries that occurred within that timeframe prior to the time at which the patient abstract is generated will qualify for inclusion in the patient abstract. As such, the selection criteria can be used to prevent stale or old information from being included in the patient abstract.

Other possible selection criteria include minimum or maximum data values and words, phrases or other text strings that must (or must not) appear in the data value in order to qualify the data element for inclusion in the patient abstract. For example, an oral temperature greater than 100 degrees Fahrenheit or below 97 degrees Fahrenheit may indicate an infection or other problem. Accordingly, a temperature data element may have selection criteria associated with it that limits inclusion of temperature data elements in the patient abstract unless the temperature falls outside of 'normal' levels. Similarly, blood work results may include selection criteria so that normal blood work reports are not included in the abstract. For example, selection criteria may specify that blood work data should only be included in the patient abstract if the blood work indicated the presence of white blood cell types at sufficient levels to indicate an allergic or toxic reaction to medicines or chemicals or indicate a condition, such as leukemia.

Each data element may also be associated with alert criteria. The alert criteria may describe certain ranges of values that, if a particular data element satisfies those values, the data element may be of critical importance to the specialist. For example, body temperature measurement that are exceedingly high may warrant alert status.

Each object within ontology 100 may also include Boolean selection criteria that must be satisfied before the data element is included within an abstract. For example, the concept "infection" 112 includes two Boolean selection criteria: "AND x" and "AND NOT y." For the concept "infection" 112 to be included, condition "x" must be TRUE and condition "y" must be FALSE. A condition may refer to another object. For example, the "infection" concept 112 may require another concept (such as "entry point") to have been inferred as a result of some term in the order or some other concept having been inferred.

Each data element in ontology 100 can also be assigned an "always search" status. In that case, regardless of the terms included in the medical order, those data elements are always search for in the patient's medical records. For example, data elements such as blood pressure, weight, age, or procedures having occurred in the last week, could always be included in a patient's abstract. The always include requirement could be assigned to either concepts or data elements as shown in ontology 100.

Optionally, each relationship in ontology 100 may be assigned a weight. For example, in ontology 100 represented in FIG. 1, the relationship 108 between "abdominal pain" 102 and "abscess" 104 has a weight w=0.75. Weights may be allocated according to an arbitrary scale, such as floating-point numbers between zero and one (0.00 to 1.00), or any other suitable continuous or discrete scale. A relationship's weight may represent a strength of the relationship between the two related objects, i.e. the weight may quantify a level of certainty that the inclusion of the first object (term) in a medical order (or the inference of the first object from a medical order) indicates that the second object should be inferred from the medical order.

In one implementation, only relationships having weights that exceed a threshold value are used to draw inferences. In that case, to draw inferences using objects in a chain of relationships, such as the chain between the term "abdominal pain" 102 and concept "infection" 112 in ontology 100, the average of the weights between pairs of the objects in the chain must exceed a threshold value. The threshold value(s) may be predetermined or dynamically set, such as based upon a sensitivity parameter that is set by a user or system administrator. In other implementations, the weight values are multiplied together to identify objects selected from the ontology that are to be used in generating the patient abstract. For example, when moving along a chain of related concepts, the system first verifies that the weighting between the first two objects exceeds a particular threshold. If so, the system then multiplies the first two weightings along the chain between the first three objects together and determines whether the multiplied value exceeds the threshold. If so, then the first three objects are valid and will be used in generating the abstract. Then, the system moves on to multiply the first three weightings between the first four objects in the chain together and determines whether the result exceeds the threshold. This process repeats until the multiplied value of the weightings no longer exceeds the threshold. At that point, the system only includes objects selected from the portion of the chain for which the multiplied weightings exceeded the threshold, ignores the remaining objects and moves on to the next chain.

The weightings may also be adjusted based upon a status of the medical order. If the order is an emergency order, the weightings could be adjusted to generate a patient abstract that is much more focused on the particular issues that are being faced by the specialist. Older information, or information that is only slightly related to the questions at hand could be excluded from the abstract to allow the specialist to quickly focus on the most relevant information possible. Alternatively, if the order indicates the presence of idiopathic symptoms, for example, the weightings can be adjusted to include more information in a particular abstract. That way additional information that may otherwise have been excluded can be presented to the specialist, but which may ultimately be relevant to making a determination as the source or cause of the symptoms.

In one implementation, a single ontology can be developed for use in generating patient abstracts for a number of different specializations. Because different objects within the ontology may have different levels of relevance to different specialties, though, different weighting systems can be developed for the different specialties. For objects that are of lesser relevance to a particular specialty, the weighting for those objects can be reduced, while the weightings for objects that are relevant can be increased. As described below, the present system allows for a specialist reviewing a particular patient abstract to provide feedback on the usefulness of the information presented in the abstract. The feedback can then be used to modify and adjust the weighting system for that specialty accordingly.

In another implementation, given a particular set of input terms, certain data elements may be indicated being mandatory before a particular abstract can be generated. If, for example, a particular written order asks a specialist to analyze some blood test results, the system will only generate a patient abstract for the specialist if the results of that blood test can be found in the patient's medical history. If the results cannot be found—perhaps because the test has not be run yet—the processing of the patient abstract will be put into a hold state until the test results are available. This avoids wasted time that a specialist would otherwise take to find test results that haven't been generated yet.

Optionally, one or more of the objects may each include one or more hyperlinks, exemplified by a hyperlink 130, to sources of related information stored in locations other than the patient's medical records. The hyperlinks may be pointers to explanations of the relevance of concepts or data elements to terms or concepts; medical texts, treatises, articles or the like or portions thereof that provide background information on various concepts; contact information (e.g., links to web pages, email addresses, or other contact information) for laboratories, service providers or people who may be consulted in relation to a particular subspecialty; policies and procedures related to diagnosis or treatment of related conditions; information about related medical procedures; reporting requirements for related diseases, such as HIV and AIDS; or the like. Some or all of the sources may be co-located with the ontology; however, some or all of the sources may be located within, and managed by, other organizations or entities. Exemplary sources include the National Library of Medicine maintained by the National Institutes of Health and the Public Health Image Library maintained by the Centers for Disease Control and Prevention.

Patient Abstract Generator

Figure 2:
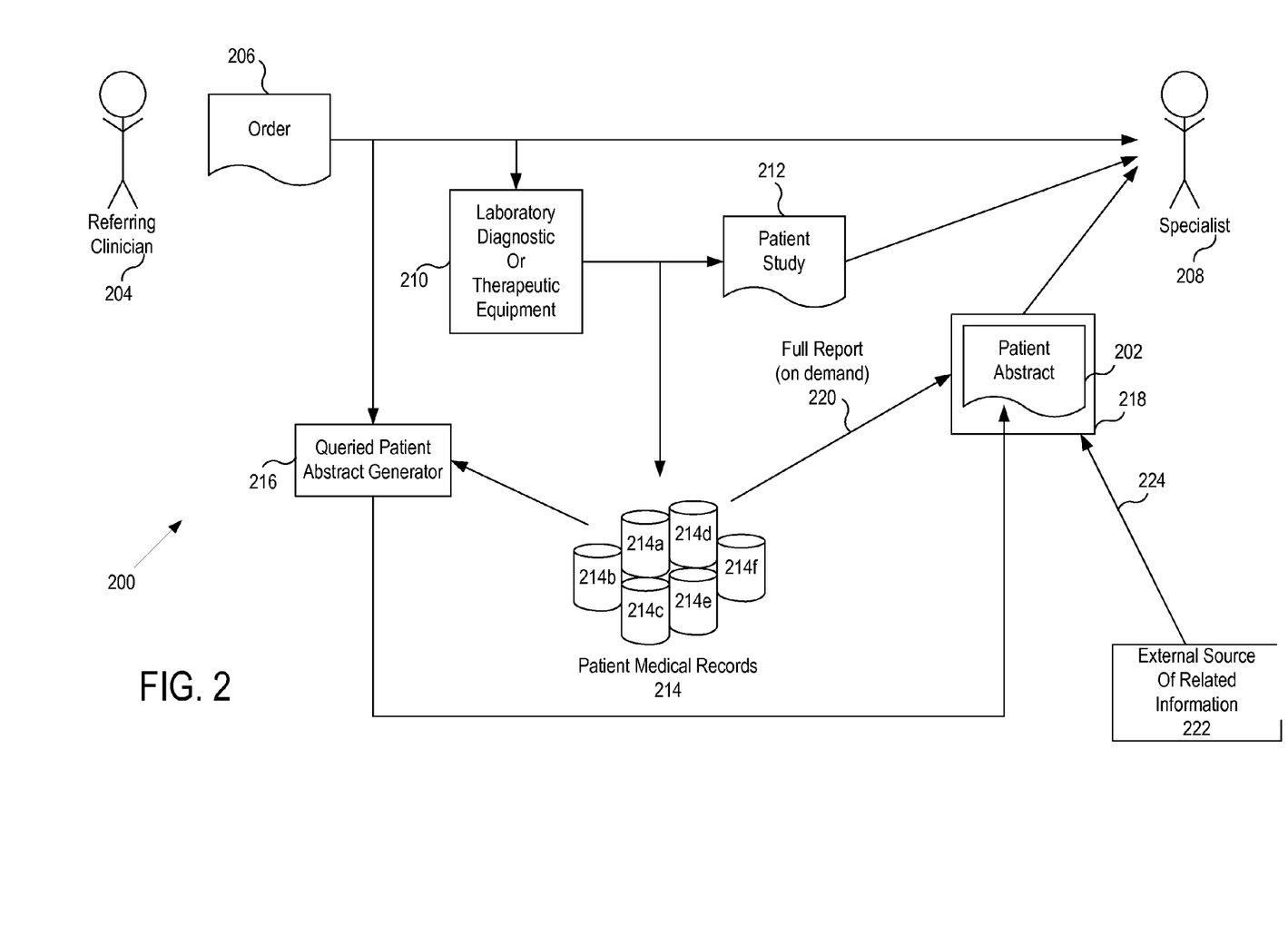
FIG. 2 is a block diagram showing functional components of a computerized system configured to generate a patient abstract.

Referring now to FIG. 2, an exemplary embodiment of a computerized system 200 for generating a queried patient abstract 202 is shown. A referring clinician 204 issues a medical order 206 to a specialist 208 for a patient (not shown). Referring clinician 204 may seek an opinion from specialist 208 regarding whether the patient has an infection, for example. Some or all of the tests, procedures, etc. listed in the order may be performed essentially immediately, i.e., within minutes of the order being written, and some or all of the tests, procedures, etc. may be performed later, such as days or weeks later. Typically, at least hours, and more typically days, pass between medical order 206 being written and issued and specialist 208 taking up the requested study 212 or performing other activities called for by medical order 206.

Laboratory, diagnostic and/or therapeutic equipment 210 is typically involved in executing procedures called for by medical order 206. In the example of a suspected infection, the equipment 210 may include blood analysis equipment designed to culture a blood sample and detect one or more strains of infectious bacteria. Equipment 210 may also be used to deliver a treatment to the patient. For example, equipment 210 may include kidney dialysis equipment. Medical order 206 may be processed manually or medical order 206 may be partially or fully automatically processed by equipment 210.

A laboratory test, such as an x-ray or a blood test, typically results in a study 212 that contains raw results of the test. The study 212 is typically delivered to the specialist 208 for analysis. As noted, this study 212 (either in its entirety or as individual data items), as well as previously performed studies, physician notes and other data about the patient, are stored in one or more databases, exemplified by databases 214a, 214b, 214c, 214d, 214e and 214f generally denoted 214. Other numbers of databases can, of course, be used. Collectively, databases 214 contain the patient's medical records 215.

Databases 214 may be of various types and sizes. Each of the databases 214 need not be in identical or compatible formats. Some data may be duplicated in more than one of databases 214. Some data may be stored "off line," such as on removable computer media, such as optical discs or magnetic tapes. Thus, accessing some of the data, or some patients' data, may take considerably more time than accessing other of the data or other patients' data. It should be noted that generating patient abstract 202 before specialist 208 takes up study 212 saves specialist 208 time, because specialist 208 need not formulate a query nor wait for databases 214 to respond.

After order 206 is written and submitted, queried patient abstract generator 216 reads order 206 and queries the patient's medical records 214 for data elements that may be relevant to the analysis or treatment that specialist 208 is to perform or provide. Abstract generator 216 uses terms in order 206 to infer concepts and to identify relevant data elements. Abstract generator 216 may use an ontology, as discussed above with reference to FIG. 1. Abstract generator 216 then generates queries of databases 214 for the identified data elements, and abstract generator 216 produces patient abstract 202 by compiling data returned as a result of the queries. A more detailed description of the operation of abstract generator 216 is provided below.

When specialist 208 begins working on the medical order, or is preparing to do so, specialist 208 may review patient abstract 202 on a computer screen 218. As noted, the elements of patient abstract 202 may be displayed with one or more hyperlinks that allow specialist 208 to access more complete data in one or more of databases 214. If specialist 208 finds an element of patient abstract 202 that is of particular interest, or for some other reason the specialist 208 wishes to review additional data from the patient's medical record 215 that is related to an element of the patient abstract 202, the specialist 208 may invoke the associated hyperlink, and the system displays the related portion of the patient's medical records 215 on the computer screen 218, as indicated by an arrow 220.

Optionally, if a term, concept or data element object that at least in part caused a particular data item to be included in the abstract 202 includes a hyperlink to an external source 222 of related information stored in a location other than the medical records, the specialist 208 may invoke the hyperlink, and the related information is fetched and displayed on the computer screen 218, as indicated by an arrow 224.

Figure 3:
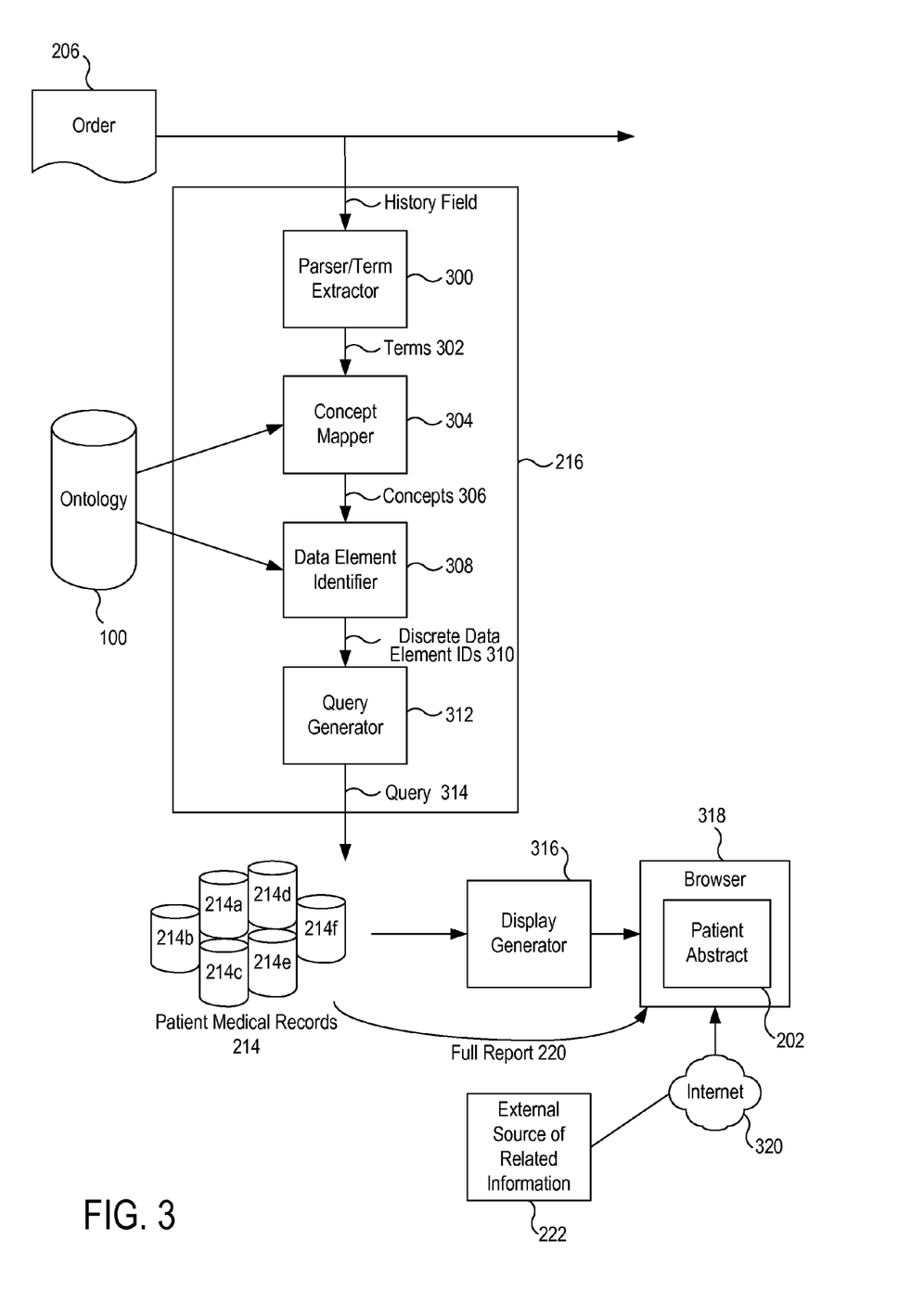
FIG. 3 is a block diagram showing components of a patient abstract generator as shown in FIG. 2.

Referring now to FIG. 3, the exemplary abstract generator 216 of FIG. 2 includes a number of components that progressively process information extracted from medical order 206 to generate one or more queries of the patient medical records 215.

The first component of the abstract generator 216, a parser/term extractor 300, reads all or a portion of the order 206 to extract terms (sometimes referred to herein as the "extracted terms"). In some implementations, the extractor 200 reads a history field or other field in the order 206 that includes the question presented by the referring clinician 204. When order 206 is handwritten, parser/term extractor 300 may include a scanner and optical character recognition (OCR) system for scanning an image of order 206 and converting the image of order 206 into a machine-readable text format. In one implementation, the scanner first scans a digital image of order 206 into an electronically-readable memory. The OCR system then accesses the electronically-readable memory and converts at least a portion of the digital image of order 206 into machine-readable text by converting the imaged letters of order 206 into their corresponding ASCII codes, or any other machine-readable code for representing the content of order 206.

The fields of the order 206 are typically not written according to a rigorous vocabulary or protocol. In addition, some or all of the fields in the order 206 may have been entered by a secretary or other non-medical person transcribing information dictated by the referring clinician 204. Thus, terms may be misspelled, abbreviated or inconsistently used. Furthermore, more than one term may be used in a single order 206 or across several orders to refer to a single concept.

The extractor 200 parses the field(s) input from the order 206 to ignore "noise" words, such as "and" and "or," to extract likely relevant terms. The extractor 300 may include a predefined list of key terms to be extracted, if any of the terms are found in the order 206. Optionally, the list of key terms may include common misspellings of terms and/or the extractor 300 may include an automatic spelling corrector. Optionally or alternatively, the extractor 300 may include a predefined list of noise words, which are not to be extracted. Extracted terms 302 are passed to the next component of the abstract generator 216.

Concept mapper 304 infers concepts 306 from the extracted terms 302, as discussed above, using an ontology such as that illustrated in FIG. 1. Inferring concepts 306 from the extracted terms 302 is also referred to as "mapping" the extracted terms 302 to the concepts 306. In some implementations, the concept mapper uses an ontology 100 (see, for example, FIG. 1); however, in other embodiments, the concept mapper 304 may use a relational, flat or other type of database, in-memory data structures similar to the blocks shown in FIG. 1 or any other suitable data store or data structures to store information about term-to-concept relationships.

When using an ontology, the system first identifies terms within the ontology that match terms retrieved from the medical order. Then, those matched terms are used to navigate the ontology to identify related concepts. As discussed above, the identification of concepts associated with particular terms may involve verifying that the weight of the relationship between the term and the identified concept exceeds a particular threshold. When numerous terms or concepts are related though a chain, this process may involve combining the associated weight of objects in the chain (e.g., via averaging, multiplication, or other methods) to verify that the weighting of the related terms and concepts is sufficiently high.

Data element identifier 308 identifies data elements 310 from the inferred concepts 306, as discussed above, with respect to FIG. 1. Identifying data elements 310 from the concepts 306 is also referred to as mapping the concepts 306 to the data elements 310. In some implementations, the data element identifier 308 uses an ontology such as ontology 100 shown in FIG. 1; however, in other embodiments, the data element identifier 308 may use a relational, flat or other type of database, in-memory data structures similar to the blocks shown in FIG. 1 or any other suitable data store or data structures to store information about concept-to-data element relationships.

When using an ontology, the system first identifies data elements that are related to the concepts identified in the preceding steps. As discussed above, the identification of data elements associated with particular concepts may involve verifying that the weight of the relationship between the concept and the identified data element exceeds a particular threshold. When numerous concepts or data elements are related though a chain, this process may involve combining the associated weight of objects in the chain (e.g., via averaging, multiplication, or other methods) to verify that the weighting of the related concepts and data elements is sufficiently high.

Query generator 312 generates one or more queries 314 to one or more of the databases 214, based upon the identified data elements 310. Each query is formulated according to syntax, access credential, communication or any other requirements of the respective database 214a-f that is queried. For example, if one of the databases 214 is a relational database (RDB), a structured query language (SQL) query may be generated. The queries may conform to the Health level 7 (HL7) protocol. If one or more of the databases 214 includes security features, such as features to make the database compliant with the Health Insurance Portability and Accountability Act (HIPAA), the query may include a username, password and/or other appropriate credentials or safeguards. If one or more of the databases 214 is remote from the abstract generator 216, the query may be sent via the Internet or another appropriate local or wide-area, public or private network, such as the Internet, a virtual private network link or other suitable network connection.

Display generator 316 receives results of the query or queries 314 and generates displayable data. This data may be displayed by a purpose-build computer application or by a general-purpose application, such as a browser 318. If the data is to be displayed in a browser 318, the data may be formatted according to a markup language, such as the Hypertext Markup language (HTML).

As noted, additional portions, or all of, the medical records 214 may be displayed by the display application or made accessible via the display. The display application, such as the browser 318, may retrieve the additional information, as indicated by an arrow 220, from the medical records 215 stored in the databases 214 for display.

Also as noted, objects in the ontology 100 or another mechanism used to store term/concept/data element relational information may include hyperlinks to external sources of related information 222. The display generator 316 may include such hyperlinks in the displayable data in relation to data elements that were selected for inclusion in the patient abstract 202. A display application, such as the browser 318, may fetch the related information 222, such as via the Internet 320.

Figure 4:
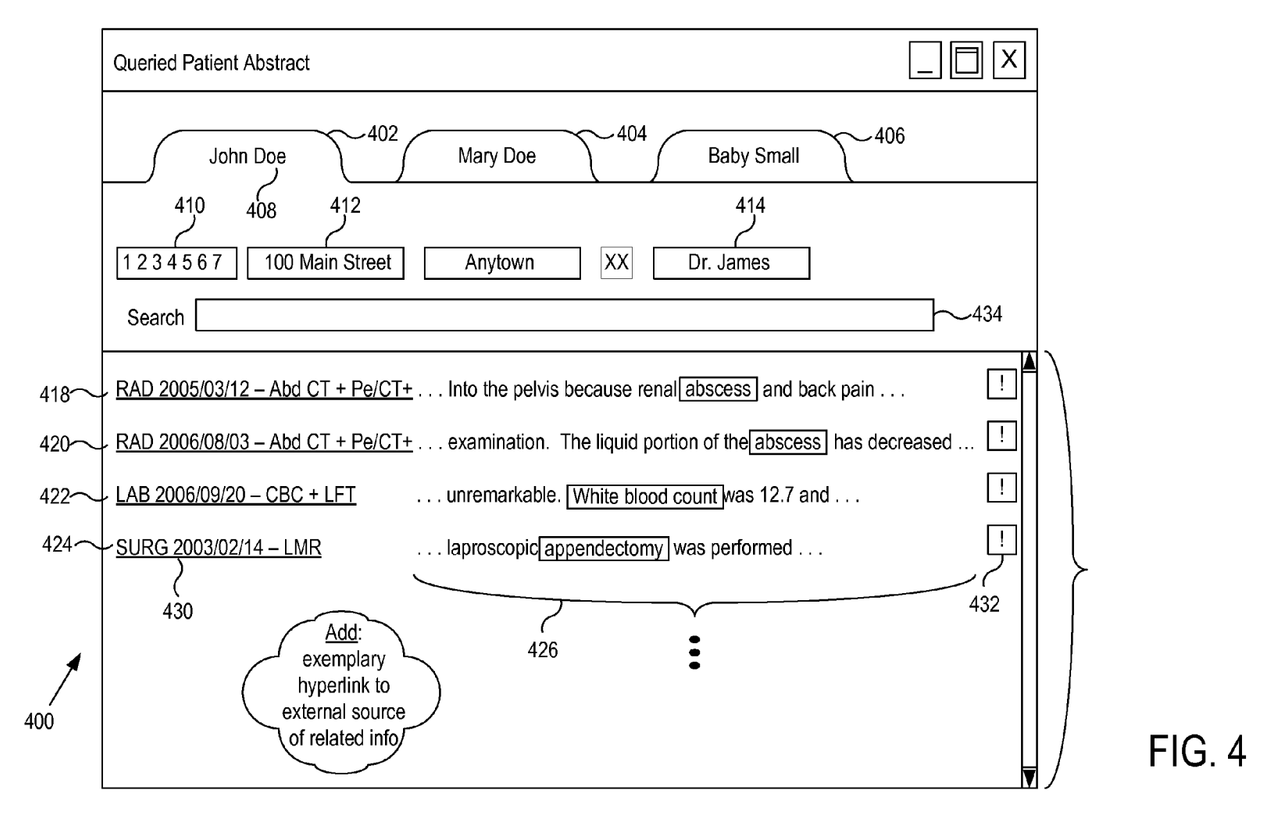
FIG. 4 is an illustration of a user interface screen displaying the results of a queried patient abstract.

Referring now to FIG. 4, an exemplary screen display 400 of a queried patient abstract 202, is shown. To facilitate a specialist's work flow, the screen display 400 may include multiple tabs, exemplified by tabs 402, 404 and 406, each of which corresponds to a different patient. For each patient, the display 400 includes patient information, such as a patient name 408, patient identification number 410, patient address 412 and referring clinician name 414.

A main portion 416 of the display 400 includes a scrollable display of data elements, exemplified by data elements 418, 420, 422 and 424, that were returned by the medical records databases 214 in response to the queryor queries 314 (FIG. 3) generated by the query generator 312. If an alert is associated with any of the data elements, the specialist can be notified via warning 432. The order in which the data elements 418-424 are displayed may be automatically chosen according to weights associated with the terms, concepts and/or data element identifiers (see FIG. 1) that were used by the extractor 300 (FIG. 3), the concept mapper 304 and the data element identifier 308 to select the data elements for the abstract 202. For each displayed data element 418-424, a portion of the medical records 214 surrounding the identified data element is displayed, as exemplified at 426. The identified data element is highlighted, as shown at 428, and a hyperlink 430 to the underlying medical record is displayed.

Optionally, the display includes a search field 434. The specialist 208 may enter a word or phrase in the search field 434, and this word or phrase is processed by the abstract generator 216, as though the word or phrase had been extracted from the order 206. That is, concepts are inferred from the word or phrase, data elements identified and the medical records databases 214 are queried for the identified data elements, as described above. Results of the query are displayed in addition to, or instead of, the results produced as a result of extracting terms from the order 206. Thus, the specialist 208 may augment or replace the abstract produced by the system.

Optionally, the specialist 208 (FIG. 2) may provide feedback to the system to indicate usefulness of any of the items displayed in the abstract 202 (FIG. 2).

Figure 5:
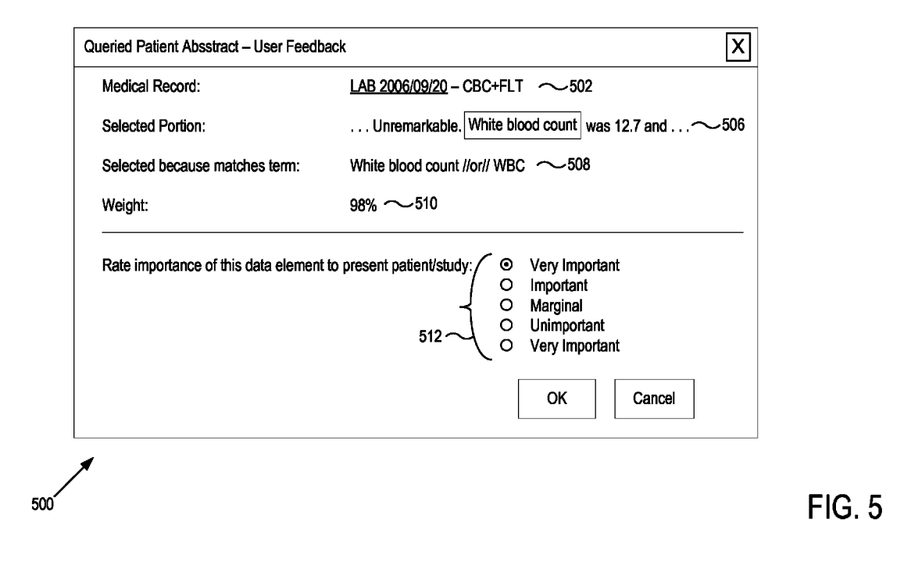
FIG. 5 is an illustration of a user interface screen allowing an operator of the user interface to provide feedback regarding usefulness of items in a patient abstract.

Referring now to FIG. 5, an exemplary screen display 500, through which the specialist may provide feedback is shown. For the selected item of the abstract 202 (FIG. 2), the screen display 500 includes a hyperlink 502 to the underlying medical record, a portion 506 of the medical records 215 that was included in the abstract 202 and information 508 about why the portion of the medical record was selected, including weight information 510, if applicable. The display 500 also includes one or more sets of choices, exemplified by choices 512, by which the specialist 208 may indicate the usefulness of the selected item.

Feedback provided via the display 500 may be used to alter the weights associated with term, concepts and/or data elements used to select the item, about which feedback has been provided. The adjustment can be made globally, so that changes to the weightings are reflected through the ontology, regardless of the specialty for which a particular abstract is being generated. Alternatively, the feedback may be used to only adjust weightings that are used in generating patient abstracts for the specialty for which the patient abstract was originally generated. This alteration may be done automatically, such as in response to each instance of feedback or in response to more than a predetermined number of instances of feedback on a single item. Optionally or alternatively, the feedback may be recorded and provided, such in a report, to a human administrator, who may then adjust the weights. If a sufficiently volume of negative feedback is generated, a system administrator may be notified, allowing the administrator to investigate the problem and determine whether the ontology, or its associated weights, requires adjustment.

Optionally, the amount of detail displayed for each item in the abstract 202 may be selected based upon a user selected parameter. In one embodiment, if the parameter indicates that the specialist 208 is an expert, less detail is displayed. However, if the parameter indicates that the specialist 208 is less experienced, more detail is displayed. The level of expertise of a particular specialist can be implemented as a multiplier assigned to the weights associated with the ontology for that specialty.

Although the abstract 202 has been described as being displayed on a computer screen, other embodiments of the present invention produce the abstract in printed form. Obviously, hyperlinks may not be invoked on a printed document; however, references to additional information may be included in a printed document, such as via footnotes.

As noted, the relationships among terms, concepts and data elements, including their weights, may be adjusted over time, such as in response to new medical knowledge. For example, ulcers were at one time thought to be related to stress, but they are now known to be an infectious disease. As a result of this new knowledge, associations and weights of associations among terms, concepts and data elements related to gastric ulcers and psychology may be changed, and such associations between ulcers and helicobacter pylori infection may be created or adjusted.

Different specialists may interpret identical data in different ways. For example, fever may raise different issues in the minds of oncologists than in the minds of orthopedists. Optionally, the system includes a parameter that identifies the specialist's specialty and uses different weights, based upon the specialty, so as to include potentially different data items in the abstract.

Other uses of the disclosed systems and methods include scheduling intervention procedures, ensuring adherence to protocols for intervention procedures and preparing primary care physicians for patients attending office visits without referrals. In the latter case, the abstract is generated from the physician's schedule, not based upon an order.

Figure 6:
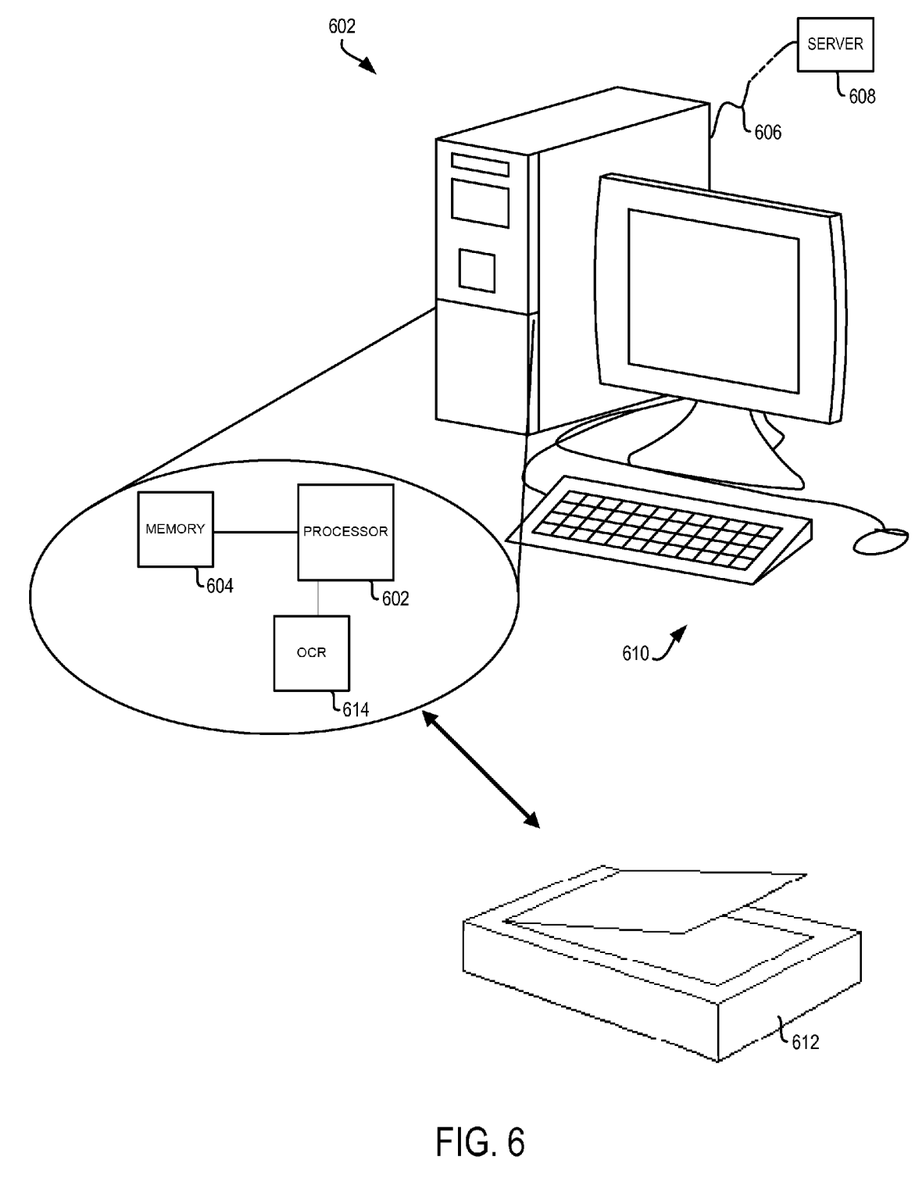
FIG. 6 is an schematic of a computer system that may be used to generate patient abstracts in accordance with the present disclosure.

FIG. 6 is an illustration of an example computer system that may be used to generate patient abstracts in accordance with the present disclosure. Computer system 600 includes processor or processing unit 602. Processor 602 is controlled by instructions stored in memory 604. Memory 604 may be random access memory (RAM), read-only memory (ROM), flash memory or any other memory, or combination thereof, suitable for storing control software or other instructions and data. Computer 600 includes communication connection 606 for communicating with one or more external computer system such as servers, database, or other data stores that may contain a patient's medical record via an electronic communications network. Computer 600 is also in communication with data storage or memory 608 upon which an ontology, as described above, may be stored. In other implementations, though, the ontology can be stored on memory 604. Computer 600 is connected to user interface 610 for displaying information to a user and receiving input (e.g., feedback) from the user. Some of the functions performed by the processors and databases have been described with reference to flowcharts in the present disclosure.

In some implementations, computer system 600 is in communication with scanner 612. For example, when processing a medical order that was originally written by hand, scanner 612 can scan an image of the medical order which can then be stored in memory 604. After being stored in memory 604, OCR system 614 can then access memory 604 can convert at least a portion of the image into machine-readable text data (e.g., ASCII strings) that can then be processed by processor 602.

Figure 7:
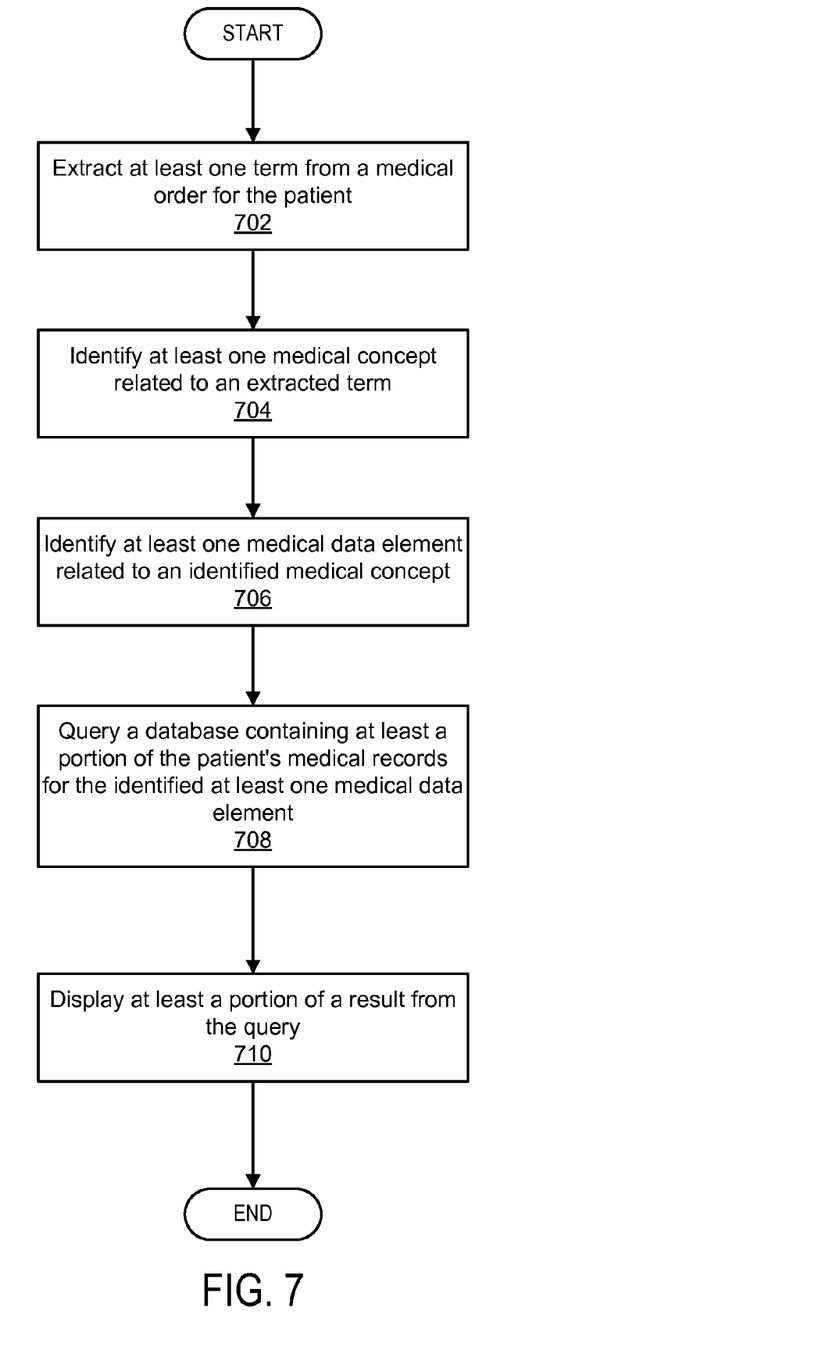
FIG. 7 is a flow chart setting forth the steps of one example method that may be implemented by the computer system of FIG. 6 for implementing the present patient abstract generator.

FIG. 7 is an illustration of one example method that may be implemented by the computer system of FIG. 6 for implementing the present patient abstract generator. In step 702, the system extracts at least one term from a medical order for the patient. The medical order can be received via a user interface, for example. In step 704, the system identifies at least one medical concept related to an extracted term, and in step 706 the system identifies at least one medical data element related to an identified medical concept. In step 708 the system queries a database containing at least a portion of the patient's medical records for the identified at least one medical data element. In step 710, the system displays at least a portion of a result from the query.

Those of ordinary skill in the art should readily appreciate that functions, operations, decisions, etc. of all or a portion of each block, or a combination of blocks, of the flowcharts may be implemented as computer program instructions, software, hardware, firmware or combinations thereof. Those of ordinary skill in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including computer networks. In addition, while the invention may be embodied in software, the functions necessary to implement the invention may alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with various illustrative data structures, one skilled in the art will recognize that the system may be embodied using a variety of data structures. Furthermore, disclosed aspects, or portions of these aspects, may be combined in ways not specifically listed above. Accordingly, it is felt therefore that the scope of protection provided by this patent should not be viewed as limited by the above description, but rather should only be limited by the scope of the below claims.

The invention claimed is:

1. A computer system for generating a patient abstract containing data about a patient selected from the patient's medical records, the computer system comprising:
   a network connection connecting the computer system to an electronic communications network to which a plurality of databases are connected, each database of the plurality of databases containing a corresponding portion of the patient's medical records;
   a scanner that generates an image of a medical order for the patient;
   electronically-readable memory storing program instructions and an ontology, the ontology including:
      a plurality of terms including a first term;
      a plurality of medical concepts including a first medical concept associated with the first term;
      a first weight that quantifies a level of certainty that the first medical concept is related to the medical order when the first term appears in the medical order;
      a plurality of data elements including a first data element associated with the first medical concept; and
      a second weight that quantifies a level of certainty that the first data element is related to the medical order when the first medical concept is related to the medical order;
   a character recognition system in communication with the scanner and the electronically-readable memory and configured to:
      convert the image of the medical order into machine-readable text and
      store the machine-readable text in the electronically-readable memory;
   a processor in communication with the electronically-readable memory, the processor executing the program instructions to:
      extract the first term from the machine-readable text;
      determine that a combination of the first weight and the second weight indicates that the first data element is related to the medical order;
      generate a first query and a second query each based on the first data element, the first query corresponding to a first database of the plurality of databases, and the second query corresponding to a second database of the plurality of databases;
      send, via the electronic communications network, the first query to the first database and the second query to the second database;
      receive, from the first database and the second database, data contained in the patient's medical records and associated with the first data element;
      generate the patient abstract such that the patient abstract includes the data and is displayable by a display application of a user device; and
      deliver the patient abstract to the display application.

2. The computer system of claim 1, wherein the processor further executes the program instructions to:
   receive input data comprising feedback from a user of the user device, the feedback indicating a usefulness of the data retrieved from the medical records; and
   modify, based on the feedback, one or both of the first weight and the second weight.

3. The computer system of claim 1, wherein to determine that the first data element is related to the medical order,
   the processor executes the program instructions to determine that an average of the first weight with the second weight exceeds a threshold value.

4. A computer-implemented method for distributing data about a medical history of a patient over a network to a display device of a specialist, the method comprising:
   converting a medical order for the patient into machine-readable text;
   extracting a first term from the machine-readable text;
   accessing an ontology stored in an electronically-readable memory, the ontology defining relationships between a plurality of terms, a plurality of medical concepts, and a plurality of data elements;
   determining that the ontology relates a first medical concept of the plurality of medical concepts to the first term with a first weight that quantifies a level of certainty that the first medical concept is related to the medical order when the first term appears in the medical order;
   determining that the ontology relates a first data element of the plurality of data elements to the first medical concept with a second weight that quantifies a level of certainty that the first data element is related to the medical order when the first medical concept is related to the medical order;
   determining, from one or both of the first weight and the second weight, that the first data element is related to the medical order;
   obtaining, from one or more of a plurality of databases containing medical records of the patient, data of the medical records that is associated with the first data element;
   generating a patient abstract that includes the data; and
   sending the patient abstract over the network to the display device.

5. The method of claim 4, wherein generating the patient abstract comprises creating a first hyperlink in the patient abstract, the first hyperlink displaying the first data element and, when invoked by the specialist via user input on the display device, connecting the display device to one or more of the plurality of databases.

6. The method of claim 4,
wherein determining that the ontology relates the first medical concept to the first term comprises comparing the first weight to a first threshold.

7. The method of claim 6, wherein determining that the first medical concept is related to the first term comprises determining that each medical concept of the plurality of medical concepts is related, by the ontology, to the first term, and
wherein determining that the plurality of medical concepts is related to the first term comprises comparing at least one of an average and a multiple of a plurality of weights associated with the plurality of medical concepts to a second threshold.

8. The method of claim 6,
wherein determining that the first data element is related to the first medical concept comprises comparing the second weight to a second threshold.

9. The method of claim 4, further comprising:
receiving, from the display device via the network, feedback indicating a usefulness of the data in the patient abstract; and
modifying, based on the feedback, one or both of the first weight and the second weight.

10. A computer-implemented method for generating a patient abstract containing data about a patient selected from the patient's medical records, the method comprising:
extracting at least one term from an electronically-readable medical order for the patient;
identifying, in an electronically-readable first database, a first medical concept related to an extracted term by a first weight stored in the first database, the first weight quantifying a level of certainty that the first medical concept is related to the medical order when the extracted term appears in the medical order;
identifying, in the first database, a first medical data element related to the first medical concept by a second weight stored in the first database, the second weight quantifying a level of certainty that the first data element is related to the medical order when the first medical concept is related to the medical order;
determining, from one or both of the first weight and the second weight, that the first medical data element is related to the medical order;
querying an electronically-readable plurality of databases, each containing at least a portion of the patient's medical records, for the first medical data element;
receiving, from one or more of the plurality of databases in response to the querying, the data about the patient selected from the patient's medical records;
generating the patient abstract containing the data; and
sending the patient abstract to a user interface that displays the patient abstract to a specialist.

11. The method of claim 10, wherein:
generating the patient abstract comprises generating a display of at least one hyperlink; and the method further comprising:
receiving an invocation of one of the displayed hyperlinks; and
updating the user interface to display a previously undisplayed portion of the patient's medical records.

12. The method of claim 10,
wherein identifying the first medical concept comprises comparing the first weight to a threshold.

13. The method of claim 10,
wherein identifying the first medical data element comprises comparing the second weight to a threshold.

14. The method of claim 10, wherein determining that the first medical data element is related to the medical order comprises determining that an average of the first weight with the second weight exceeds a threshold value.

* * * * *